United States Patent [19]
Howard

[11] Patent Number: 6,013,085
[45] Date of Patent: Jan. 11, 2000

[54] METHOD FOR TREATING STENOSIS OF THE CAROTID ARTERY

[76] Inventor: John Howard, 2711 Flintgrove Rd., Charlotte, N.C. 28226

[21] Appl. No.: 08/966,279

[22] Filed: Nov. 7, 1997

[51] Int. Cl.[7] ................................................. A61M 25/10
[52] U.S. Cl. ........................... 606/108; 606/194; 604/96; 604/101
[58] Field of Search .................................... 606/108, 194; 604/101, 96

[56] References Cited

U.S. PATENT DOCUMENTS

| | | |
|---|---|---|
| 4,295,464 | 10/1981 | Shihata . |
| 4,748,982 | 6/1988 | Horzewski et al. ................. 604/102 X |
| 4,911,163 | 3/1990 | Fina ..................... 606/108 X |
| 5,059,178 | 10/1991 | Ya . |
| 5,180,367 | 1/1993 | Kontos et al. ........................... 604/101 |
| 5,192,297 | 3/1993 | Hull . |
| 5,281,200 | 1/1994 | Corso, Jr. et al. . |
| 5,370,617 | 12/1994 | Sahota . |
| 5,423,742 | 6/1995 | Theron . |
| 5,439,446 | 8/1995 | Barry . |
| 5,456,694 | 10/1995 | Marin et al. . |
| 5,458,605 | 10/1995 | Klemm . |
| 5,484,412 | 1/1996 | Pierpont . |
| 5,501,668 | 3/1996 | Kontos ....................................... 604/96 |
| 5,591,198 | 1/1997 | Boyle et al. . |
| 5,599,307 | 2/1997 | Bacher et al. . |
| 5,807,330 | 9/1998 | Teitelbaum ................................ 604/96 |

FOREIGN PATENT DOCUMENTS

| | | |
|---|---|---|
| 0 279 959 A1 | 12/1987 | European Pat. Off. ........ A61M 25/00 |
| 0 551 184 A1 | 1/1993 | European Pat. Off. ........ A61M 29/02 |
| 627828 | 10/1978 | U.S.S.R. . |
| WO 87/07510 | 12/1987 | WIPO .......................... A61M 29/02 |
| WO 95/09024 | 4/1995 | WIPO .......................... A61M 29/02 |
| WO 95/16487 | 6/1995 | WIPO .......................... A61M 31/00 |
| WO 98/26833 | 6/1998 | WIPO .......................... A61M 31/00 |
| WO 98/38930 | 9/1998 | WIPO .......................... A61B 17/22 |
| WO 98/39047 | 9/1998 | WIPO .......................... A61M 25/00 |

OTHER PUBLICATIONS

Theron et al., *Neuroadiology*, vol. 201, No. 3, "Carotid Artery Stenosis: Treatment With Protected Balloon Angioplasty and Stent Placement", (1996) pp. 627–636.

*Primary Examiner*—Michael H. Thaler
*Attorney, Agent, or Firm*—Allen, Dyer, Doppelt, Milbrath & Gilchrist, P.A.

[57] ABSTRACT

An endovascular method for treating a stenosis of a carotid artery of a patient provides cerebral protection during placement of a stent at the expanded stenosis. The method preferably comprises the steps of providing a first catheter comprising a first balloon at a distal end thereof, the catheter having a first lumen therein; and positioning the first catheter in the carotid artery of the patient so that the first balloon is downstream from the stenosis. The first balloon is inflated in the carotid artery downstream from the stenosis to block the carotid artery to provide cerebral protection for the patient and to anchor the distal end of the first catheter in the carotid artery. An elongate stiffening member may be inserted in the first lumen of the first catheter to stiffen the first catheter. Accordingly, the first catheter can then be used as a guide to position further catheters for treating the stenosis. The method may also include the steps of providing a second catheter comprising a second balloon at a distal end, and positioning the second balloon at the stenosis by sliding the second catheter over the catheter guide while cerebral protection is provided by the inflated first balloon. The second balloon may be inflated to expand the stenosis also while cerebral protection is provided by the inflated first balloon. A stent is positioned at the expanded stenosis while protection is maintained. Suction and/or lavage may then be performed also with cerebral protection.

27 Claims, 5 Drawing Sheets

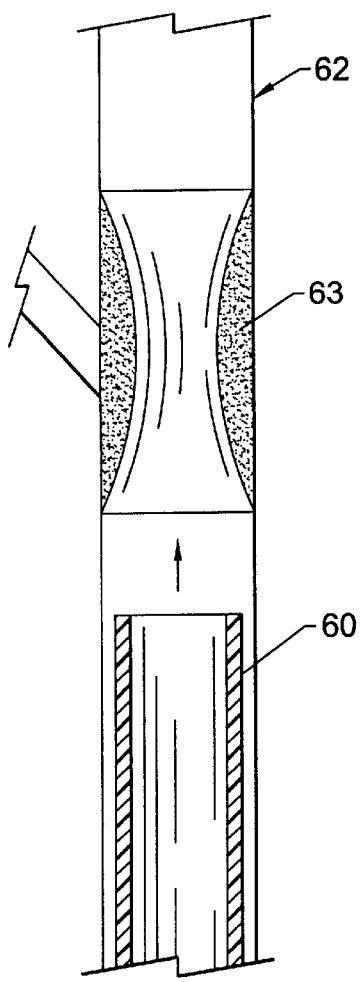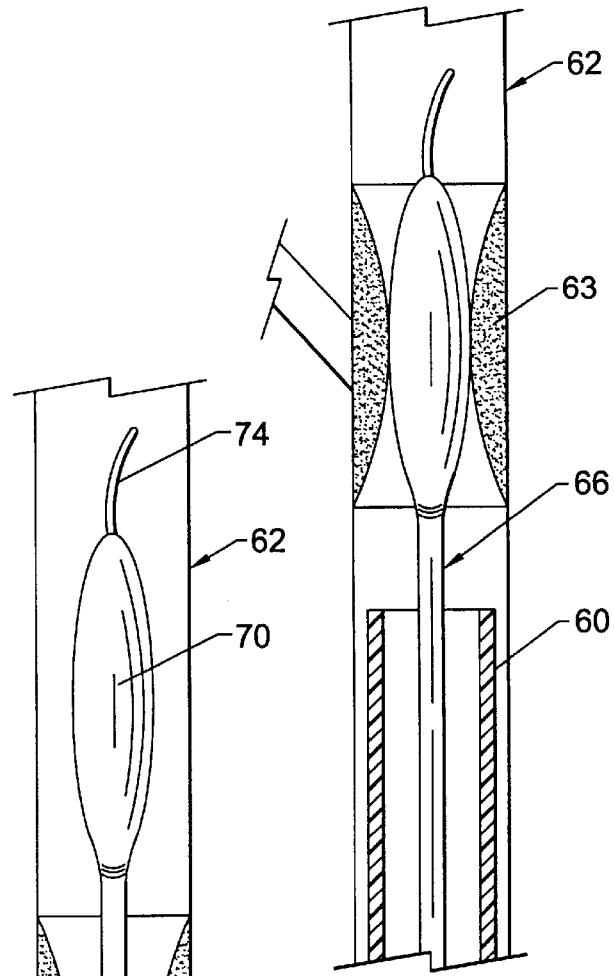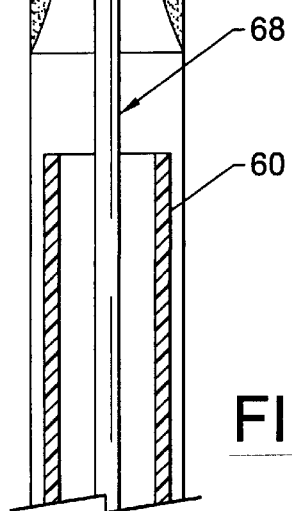

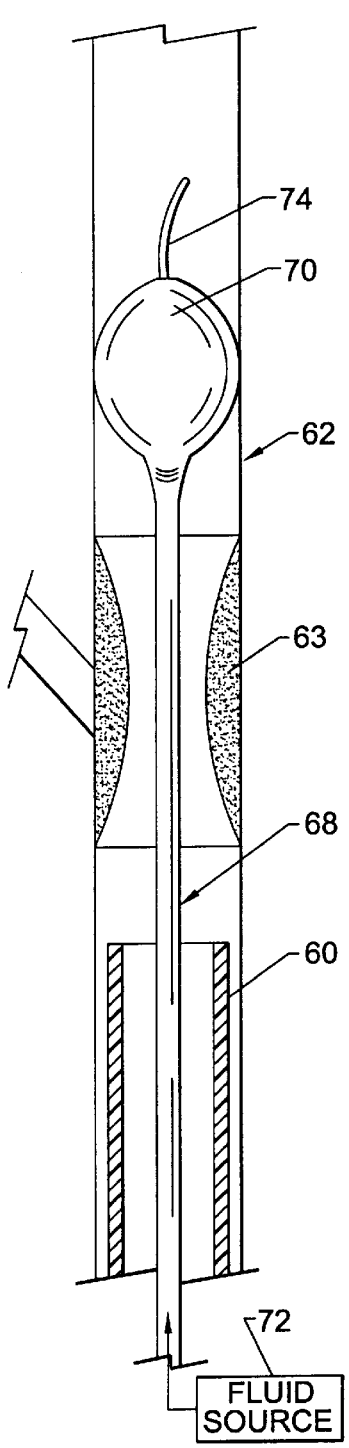
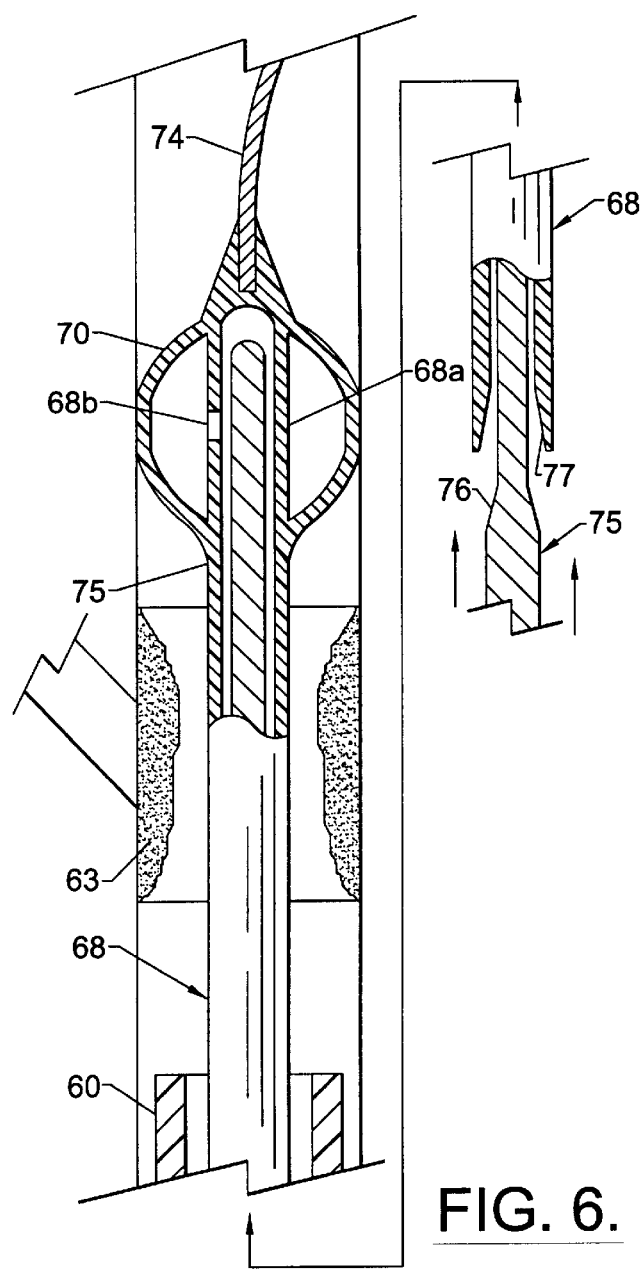
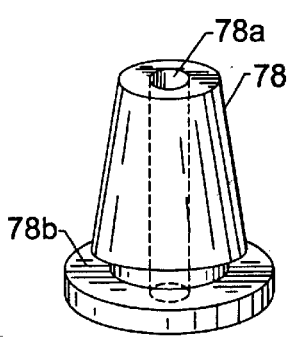
FIG. 5.
FIG. 6.
FIG. 7.

METHOD FOR TREATING STENOSIS OF THE CAROTID ARTERY

FIELD OF THE INVENTION

The present invention relates to vascular treatment techniques and apparatus, and, more particularly, to a method and system or apparatus for treating a stenosis in a large blood vessel, such as the carotid artery.

BACKGROUND OF THE INVENTION

Recent medical studies have determined that the surgical removal of atherosclerotic plaques in the carotid bifurcation region may significantly reduce the incidence of stroke. This is so for a greater than about 70% narrowing of the region for both asymptomatic and symptomatic individuals. The surgical plaque-removal technique is known as carotid endarectomy. When this procedure is performed by an experienced surgeon, that is, one performing more than about 50 procedures per year, the morbidity and mortality are approximately 5%. The most common complication of carotid endarectomy may be stroke. Accordingly, though complications are infrequent, they tend to be life altering.

The technology exists to treat stenotic lesions of the carotid bifurcation region from an endovascular approach, for example, via transarterial catheter techniques. Endovascular therapy may typically be less traumatic to the patient, and more cost effective. For endovascular treatment of carotid atherosclerotic disease (CAD) to become more widely accepted, long-term patency rates of the treated lesions and the complication rate should be as good as or better than surgical therapy.

One study evaluating endovascular treatment of CAD has been published in the medical literature as authored by J. G. Theron et al., appearing in *Radiology* 201, 627–636, 1996. This study determined that angioplasty followed by stenting decreased the incidence of restenosis and reduced the risk of carotid dissection when compared with angioplasty alone. The Theron article discloses endovascular treatment of carotid artery stenosis by angioplasty, and with cerebral protection provided by a balloon blocking the vessel downstream from the stenosis. Also, when the cerebral circulation fed by the vessel being treated was so protected, the incidence of stroke decreased. The method only allowed for cerebral protection during angioplasty, and not during the stenting procedure. In other words, stent placement is described, but without cerebral protection. The Theron article and associated U.S. Pat. No. 5,423,742 to Theron each describe a triple coaxial catheter system that enabled angioplasty with temporary carotid occlusion, aspiration of debris, and flushing of the working site.

According to the Theron approach, a guiding catheter is first positioned to extend to adjacent the stenosis, and the catheter carrying the occlusion balloon and the dilatation catheter may be guided through a central lumen of the guiding catheter in a coaxial relationship. The guiding catheter as sized for positioning in the carotid artery, had an insufficient lumen diameter relative to the size of the desired stent to allow for positioning of the stent through the guiding catheter. Consequently the cerebral protection technique could not be used at this important step of the endovascular treatment. Despite this shortcoming, the risk of embolic complication, however, was described in the Theron article as markedly reduced because preliminary angioplasty was performed with cerebral protection. Unfortunately, stent placement without protection may also cause plaque deposits to become dislodged and, thus, possibly flow downstream to the unprotected cerebrum of the patient.

While angioplasty and stent placement techniques have been developed for other blood vessels, such as the coronary arteries, for example, developments in endovascular treatment for the carotid artery have lagged. U.S. Pat. No. 5,484,412 to Pierpont, for example, is representative of developments for advanced techniques for treating stenosis of the coronary arteries. U.S. Pat. No. 5,439,446 to Barry discloses a stent delivery system. U.S. Pat. No. 5,281,200 to Corso, Jr. et al. discloses a balloon-on-a-wire assembly and an over-the-wire catheter which slidably passes over the balloon-on-a-wire assembly for predilatation, and subsequent dilatation, respectively.

SUMMARY OF THE INVENTION

In view of the foregoing background, it is therefore an object of the present invention to provide a relatively easy to use endovascular method and associated catheter system for treating a stenosis in the carotid artery, and while providing enhanced cerebral protection for the patient.

This and other objects, features and advantages of the present invention are provided by an endovascular method for treating a stenosis of a carotid artery of a patient, wherein cerebral protection is also provided during placement of a stent at the stenosis. More particularly, the method preferably comprises the steps of providing a first catheter comprising a first balloon at a distal end thereof, the catheter having a first lumen therein; and positioning the first catheter in the carotid artery of the patient so that the first balloon is downstream from the stenosis. The first balloon is inflated in the carotid artery to block the carotid artery to provide cerebral protection for the patient and to anchor the distal end of the first catheter in the carotid artery. According to one important aspect of the invention, an elongate stiffening member may be inserted in the first lumen of the first catheter to stiffen the first catheter. Accordingly, the first catheter can then be used as a guide to aid in positioning further catheters for treating the stenosis.

The method may also include the steps of providing a second catheter comprising a second balloon at a distal end thereof, and positioning the second balloon at the stenosis by sliding the second catheter over the catheter guide while cerebral protection is provided by the inflated first balloon. The second balloon may be inflated to expand the stenosis—also while cerebral protection is provided by the inflated first balloon. As mentioned briefly above, the method preferably includes the step of placing a stent at the expanded stenosis while cerebral protection is maintained. Suction and/or lavage may be performed to remove any debris by sliding a suction/lavage catheter over the catheter guide provided by the stiffened first catheter, and while cerebral protection is maintained. After the suction/lavage catheter is withdrawn, the first balloon may be deflated and the first catheter removed to re-establish downstream circulation.

In one variation of the invention, the first lumen is in fluid communication with the first balloon, and the step of positioning the elongate stiffening member also seals the inflated first balloon. The stiffening member may be fully inserted when initially positioning the first catheter. The elongate stiffening member may have an enlarged outer diameter at a predetermined location. Accordingly, the step of positioning the elongate stiffening member may comprise positioning same to seal a proximal end of the first lumen of the first catheter with the enlarged diameter portion.

In one embodiment, the second catheter carries a stent at the distal end so that the steps of inflating the second balloon and placing the stent may be performed simultaneously.

Alternately, the second catheter may be used for expanding the stenosis, and a third catheter used for stent placement. The stent may be self-expanding when released. Of course, cerebral protection is still readily maintained because the first balloon is inflated and the anchored first catheter serves as a guide for the additional catheters.

The method may further comprise the steps of: providing an introduction catheter having a lumen and positioning a distal end of the introduction catheter adjacent the stenosis, and inserting the first catheter through the lumen of the introduction catheter. The method may also further comprise the step of removing the introduction catheter at any time after inflating the first balloon, as the first catheter serves as a guide for subsequent positioning of the other catheters, and, particularly, the stent delivery catheter. In some embodiments, the stenosis may need to be predilatated prior to positioning the first catheter through the introduction catheter.

A catheter system aspect of the present invention is also for treating a stenosis of a carotid artery of a patient. The catheter system preferably includes a first catheter having a first lumen and comprising a first balloon at a distal end thereof for being positioned in the carotid artery of the patient so that the first balloon is downstream from the stenosis. The first balloon is inflatable in the carotid artery downstream from the stenosis to block the carotid artery to provide cerebral protection for the patient and to anchor the distal end of the first catheter in the carotid artery. The system may also include an elongate stiffening member insertable in the first lumen of the first catheter to stiffen the first catheter to define a catheter guide. In addition, the system may also include at least one other catheter for performing at least one procedure associated with treating the stenosis. The at least one other catheter preferably has a lumen extending therethrough for being slidably positioned over the catheter guide, and while the inflated first balloon maintains cerebral protection for the patient.

The at least one other catheter may comprise a stent delivery catheter, a dilatation catheter, or a suction/lavage catheter. The system may also include an introduction catheter for being positioned adjacent the stenosis and for receiving the first catheter therethrough. The first catheter preferably comprises a lubricious outer coating, and the at least one other catheter may also include a lubricious inner coating. The catheter system in accordance with the present invention facilitates treatment of a stenosis at the carotid artery, and, in particular, provides cerebral protection during placement of the stent.

BRIEF DESCRIPTION OF THE DRAWINGS

FIG. 2 is a side cross-sectional view of a carotid artery and catheter system showing positioning of an introduction catheter in accordance with the present invention.

FIG. 3 is a side view, partially in section, of the carotid artery and catheter system showing predilatation of the stenosis in accordance with the present invention.

FIG. 4 is a side view, partially in section, of the carotid artery and catheter system showing positioning of a first catheter and its first balloon dowmstream from the stenosis in accordance with the present invention.

FIG. 5 is a side view, partially in section, of the carotid artery and catheter system showing inflation of the first balloon of the first catheter positioned as shown in FIG. 4 and providing cerebral protection.

FIG. 6 is an enlarged side view, partially in section, of the carotid artery and catheter system showing insertion of an elongate stiffening member into the first lumen of the first catheter positioned as shown in FIG. 5, while cerebral protection is provided.

FIG. 7 is an enlarged perspective view of a hub insertable into the proximal end of the first catheter in accordance with the present invention.

DETAILED DESCRIPTION OF THE PREFERRED EMBODIMENTS

The present invention will now be described more fully hereinafter with reference to the accompanying drawings, in which preferred embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. Like numbers refer to like elements throughout.

Figure 1:
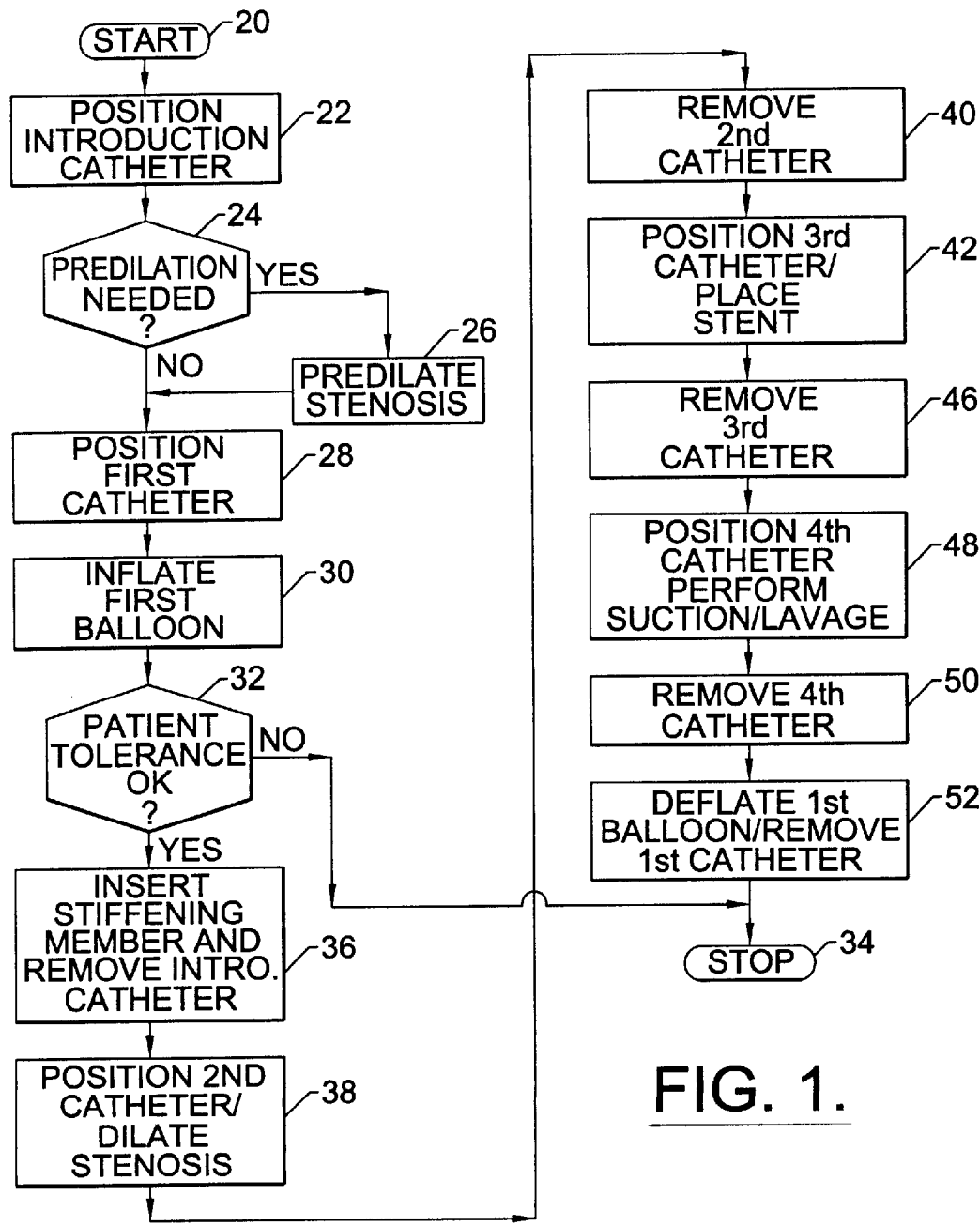
FIG. 1 is a flow chart illustrating the method steps in accordance with the present invention.

The method of the present invention is explained with reference to the flow chart of FIG. 1 and the accompanying sectional views of FIGS. 2–11. One aspect of the invention is directed to an endovascular method for treating a stenosis of a carotid artery of a patient. From the start (Block 20), an introduction catheter 60 is inserted into the carotid artery 62 to adjacent the carotid bifurcation region at Block 22 using conventional techniques as also shown in FIG. 2, and as would be readily appreciated by those skilled in the art. The carotid bifurcation region illustratively includes in the sectional views, a stenosis 63 or constriction defined by the formation of plaques as will also be readily appreciated by those skilled in the art. At Block 24 it is determined whether predilatation is needed, such as to open the stenosis sufficiently for subsequent steps. If the predilatation is needed, this is performed (Block 26) using conventional techniques and an appropriately sized predilatation catheter 66 as illustrated in the sectional view of FIG. 3, and as would be appreciated by those skilled in the art. For example, a cardiology type dilatation catheter may be used.

If predilatation is not needed, or after it has been performed, a first catheter 68 is inserted through the introduction catheter 60 at Block 28 and as shown in the sectional view of FIG. 4. The first catheter 68 illustratively includes a first balloon 70 at a distal end thereof. The first catheter 68 also has a first lumen therein. The first catheter 68 is positioned in the carotid artery 62 of the patient so that the first balloon 70 is downstream from the stenosis 63. For example, the first balloon 70 may be positioned about 5–6 cm downstream from the stenosis 63. At Block 30 and as shown in the sectional view of FIG. 5, the first balloon 70 is inflated in the carotid artery 62 downstream from the stenosis to block the carotid artery to thereby provide cerebral protection for the patient and to anchor the distal end of the first catheter 68 in the carotid artery. The first balloon 70 is inflated using conventional techniques, such as via connection to the schematically illustrated fluid source 72 as would be readily understood by those skilled in the art.

Upon inflation of the first balloon 70, blood flow is stopped downstream from the balloon. Accordingly, at Block 32 the patient is checked for tolerance of the stoppage of blood flow, and if tolerance is unacceptable, the procedure is stopped (Block 34) and other options may be considered for the patient. The patient's tolerance may be checked during other phases of the treatment as will be readily appreciated by those skilled in the art without further discussion herein.

According to one important aspect of the invention, if patient tolerance is acceptable at Block 32, then an elongate stiffening member 75 may be inserted in the first lumen 73 of the first catheter 68 to stiffen the first catheter (Block 36) and as shown in the enlarged sectional view of FIG. 6. Of course, as would be readily appreciated by those skilled in the art, the elongate stiffening member 75 may have been inserted prior to positioning the first balloon 70 downstream from the stenosis 63 to assist the first catheter in traversing the stensosis.

The introduction catheter 60 may also now be removed, or may be removed at any time after inflation of the first balloon 70. Moreover, the first catheter 68 can then be used as a guide to position further catheters for treating the stenosis. The first catheter 68, once the stiffening member 75 is inserted therein, provides a guide for other relatively stiff and poorly tracking treatment catheters, and allows the treating physician to gain access to areas through event the most tortuous vascular systems. In addition, the stiffened first catheter permits conventional stent delivery and dilatation catheters to be used as will be appreciated by those skilled in the art.

In other variations of the invention, the elongate stiffening member 75, such as a metallic wire or plastic member, may have already been completely positioned in the lumen 73 of the first catheter 68, prior to positioning of the first catheter in the carotid artery 62. The stiffening member 75 can be readily removed to facilitate inflating of the first balloon 70.

As also shown in FIG. 6, the first catheter 68 may have a guiding tip 74 extending outwardly from the distal end of the first balloon 70 to facilitate positioning as would be readily understood by those skilled in the art. The tip 74 may be a wire fused into or otherwise joined to the end of the first catheter 68. The tip 74 may have a diameter of about 0.0035 inches and a length of about 2 to 2.5 cm, for example. An outermost end portion of the tip 74 may be bent to facilitate steering. The tip 74 may assist in traversing a stenosis defining an opening of only about 1 mm, for example. The tip 74 may include an outer lubricious coating as will be readily understood by those skilled in the art. The tip 74 helps the first catheter 68 traverse the stenosis 63 and without dislodging any plaque, as would be readily appreciated by those skilled in the art.

The first catheter 68 may have about a 4 French outer diameter and be about 130 cm in overall length. The first balloon may be 70 about 2 cm long, with an outer diameter of about 4–6 mm. The first lumen 73 may be about 0.09 cm in diameter.

As shown in FIG. 6, the first catheter 68 may include an opening 68b through the sidewall of the tubular body portion 68a at the distal end and within the first balloon 70. Accordingly, the elongate member 75 may seal the first balloon 70 in the inflated position by blocking the egress of fluid from through the opening 68b. As is also understood with particular reference to FIG. 6, the elongate member 75 may include a tapered or enlarged diameter portion 76 that matingly engages and seals against a corresponding tapered proximal end portion 77 of the first catheter 68. Accordingly, in this embodiment, the elongate stiffening member 75 not only stiffens the first catheter 68 so that it may be use as a catheter guide, but also seals the first balloon 70 in the inflated position.

Referring now briefly to FIG. 7, the proximal end of the first catheter 68 may also be closed by the illustrated removable tapered hub 78 having an opening 78a therethrough to facilitate inflation of the first balloon 70 as would be readily appreciated by those skilled in the art. The tapered hub 78 may be used when the elongate member 75 is not in the first lumen 73 of first catheter 68 as during inflation of the first balloon 70. As shown in the illustrated Embodiment, the hub 78 includes a flange portion 78b to which a syringe, for example, may be connected to inflate the first balloon 70. In other embodiments as will be appreciated by those skilled in the art, a syringe or other device may be temporarily secured to outer portions of the proximal end of the first catheter 68, such as by threads, for example. The tapered hub 78, however, offers a number of advantages including ease of manufacture and ease of use.

The elongate stiffening member 75 may be about 260 cm in overall length. In addition, the elongate stiffening member 75 may have an outer diameter of about 0.08 cm at its distal portion, and about 0.135 cm at its proximal portion. The transition between the two diameters may be gradual at about the middle of the member, and this transition defines a taper that may extend about 4 cm along the member. The taper corresponds to the tapered proximal opening of the first lumen 73 of the first catheter 70.

As will also be readily appreciated by those skilled in the art, in other embodiments, the first catheter 68 may include multiple lumens, such as for receiving the stiffening member 75 through one lumen and permitting inflation of the first balloon 70 through another lumen, for example. In addition, in some embodiments of the invention, the stiffening member 75 may not be needed, as long as the first catheter 68 is sufficiently rigid by itself to serve as a guide for positioning subsequent catheters, particularly the stent placement catheter, as will be discussed in greater detail below.

Figure 8:
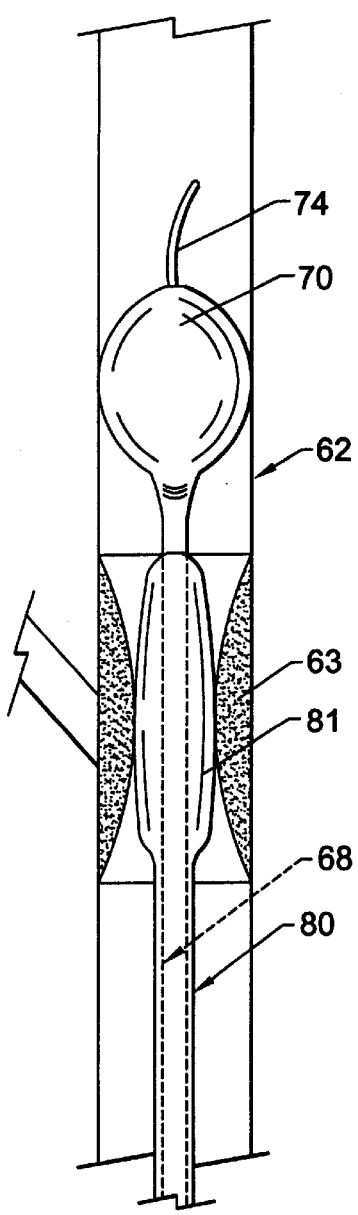
FIG. 8 is a side view, partially in section, of the carotid artery and catheter system showing dilatation of the stenosis using a second balloon of a second catheter while cerebral protection is provided in accordance with the present invention.

At Block 38 and as shown in the sectional view of FIG. 8, the method may also include the steps of providing a second catheter 80 comprising a second balloon 81 at a distal end thereof, and positioning the second balloon at the stenosis 63 by sliding the second catheter over the first catheter 68 and while cerebral protection is provided by the inflated first balloon 70. The second balloon 81 may be inflated to expand the stenosis 63 also while cerebral protection is provided by the inflated first balloon 70, and as will be readily appreciated by those skilled in the art. As noted in Block 40, the second catheter 80 may now be removed.

Figure 9:
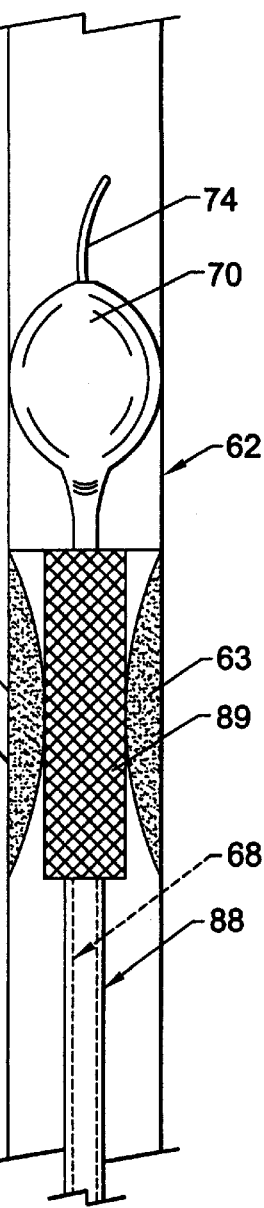
FIG. 9 is a side view, partially in section, of the carotid artery and catheter system showing stent placement while cerebral protection is provided in accordance with the present invention.

The method in accordance with one embodiment preferably includes the step of positioning a third catheter 88 over the first catheter 68 so as to permit placing a stent 89 at the expanded stenosis 63 (Block 42) and as shown in the sectional view of FIG. 9. The placement of the stent 89 may be performed while cerebral protection is maintained by the inflated first balloon 70. Accordingly, any debris generated by placing the stent 89 are retained in the area upstream of the first balloon 70 rather than permitted to flow downstream to the cerebral area of the patient.

Those of skill in the art will appreciate that the steps of expanding the stenosis 63 and positioning the stent 89 may be performed using a single catheter where the balloon is positioned inside the stent. In other embodiments, a self-expanding stent may be released from the third catheter as will be readily appreciated by those skilled in the art. The placement of the stent 89 is performed with cerebral protection, unlike the prior art attempts as described in the Theron article and corresponding U.S. patent to Theron discussed extensively above in the Background of the Invention section. The prior art Theron approach was unable to provide protection during placing of the stent, at least in part, because of a lack of compatibility between the stent placement catheter and the needed guiding or introduction catheter through which the stent placement catheter would have had to have been positioned.

Figure 10:
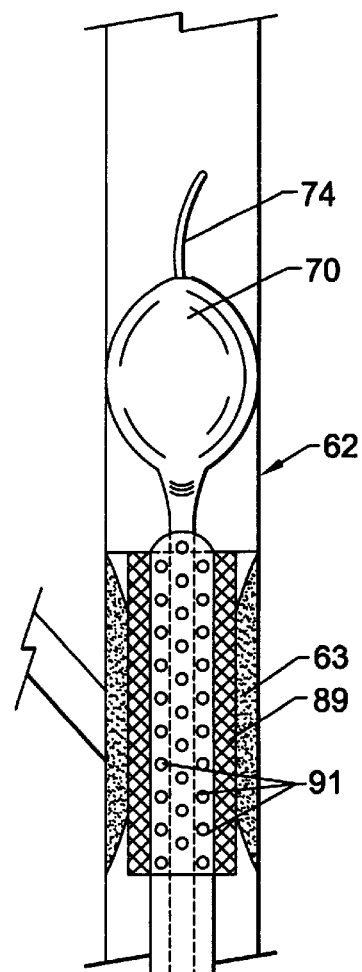
FIG. 10 is a side view, partially in section, of the carotid artery and catheter system showing positioning of a fourth catheter for performing suction/lavage while cerebral protection is provided in accordance with the present invention.

At Block 46 the third catheter 88 may be removed and at Block 48 a fourth catheter 90 for performing suction and/or lavage may then be inserted over the first catheter 68 as shown in the sectional view of FIG. 10. The illustrated suction/lavage catheter 90 is connected to a schematically illustrated source of suction or fluid 93 via a transverse flush/aspiration port 95, the operation of which would be readily understood by those skilled in the art. The suction/lavage catheter 90 includes a seal 97 at a proximal end thereof which seals to the adjacent surface of the first catheter 68 yet which permits sliding over the first catheter.

Of course, the first balloon 70 remains inflated to provide protection also during this stage which removes any unwanted debris from the area. The illustrated suction/lavage catheter 90 includes a plurality of relatively large size openings 91 in the sidewall at the distal end, and may preferably also be sealed to the first catheter 68 at its distal end to thereby permit greater suction from the openings 91. The openings 91 may be about 0.033 cm in diameter, the length of the distal working portion of the suction/lavage catheter 90 may be about 5 cm, and the outer diameter thereof may be about 0.27 cm. The suction/lavage catheter 90 may be about 130 cm in overall length and have a 7 or 8 French outer diameter. The opening at the distal end may be about 0.13 cm to permit positioning over the first catheter 68.

The fourth or suction/lavage catheter 90 may be removed at Block 50. During removal, suction may be maintained to trap any relatively large debris against the openings 91. In other words, debris may be removed by passing through the openings 91, but also may be removed when trapped against the adjacent portions of the openings.

Figure 11:
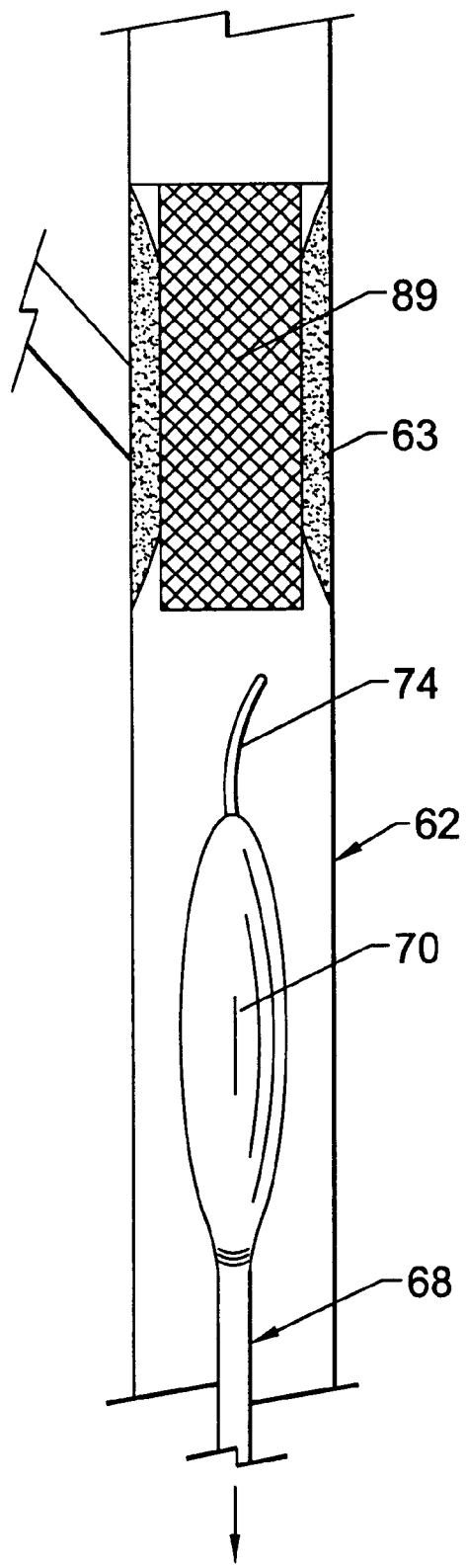
FIG. 11 is a side view, partially in section, of the carotid artery and catheter system showing removal of the first catheter upon completion of the stenosis treatment procedure.

At Block 53 and as shown in the sectional view of FIG. 11, the first balloon 70 may be deflated and the first catheter 68 may also be withdrawn. The procedure is then complete (Block 34). Accordingly, the stenosis 63 has been treated by expansion, and the stent 89 is left in place to reduce the likelihood of restenosis. Moreover, because cerebral protection is provided throughout the major steps of the procedure, including stent placement, the immediate and long term results are likely to be superior to those where no protection is provided during stent placement. In addition, the endovascular approach in accordance with the present invention is likely to be preferred over surgical techniques as well.

The first catheter 68 preferably comprises a lubricious outer coating, and the other catheters may also include a lubricious inner coating as would be readily appreciated by those skilled in the art to facilitate sliding of the outer treatment catheter over the first catheter. As will be readily appreciated from the foregoing description, the catheter system in accordance with the present invention facilitates treatment of a stenosis at the carotid artery, and while providing cerebral protection during placement of the stent 89.

While the particular method and catheter system of the present invention have been described with reference to treatment of a stenosis of the carotid artery, those of skill in the art will recognize that the invention may be adapted for similar treatment of other large diameter blood vessels. Accordingly, many modifications and other embodiments of the invention will come to the mind of one skilled in the art having the benefit of the teachings presented in the foregoing descriptions and the associated drawings. Therefore, it is to be understood that the invention is not to be limited to the specific embodiments disclosed, and that modifications and embodiments are intended to be included within the scope of the appended claims.

That which is claimed is:

1. An endovascular method for treating a stenosis of a carotid artery of a patient, the method comprising the steps of:

providing a first catheter comprising a first balloon at a distal end thereof, the catheter having a first lumen therein;

positioning the first catheter in the carotid artery of the patient so that the first balloon is downstream from the stenosis;

inflating the first balloon in the carotid artery downstream from the stenosis to block the carotid artery to provide cerebral protection for the patient and to anchor the distal end of the first catheter in the carotid artery;

inserting an elongate stiffening member in the first lumen of the first catheter after inflating the first balloon to stiffen the first catheter to define a catheter guide;

providing a second catheter comprising a second balloon at a distal end thereof;

positioning the second balloon at the stenosis by sliding the second catheter over the catheter guide while cerebral protection is provided by the inflated first balloon;

inflating the second balloon to expand the stenosis while cerebral protection is provided by the inflated first balloon;

placing a stent at the expanded stenosis while cerebral protection is maintained by the inflated first balloon; and deflating the first balloon to re-establish blood flow and withdrawing the first catheter from the patient.

2. A method according to claim 1 wherein the first lumen is in fluid communication with the first balloon, and wherein the step of positioning the elongate stiffening member also seals the inflated first balloon.

3. A method according to claim 2 further comprising the steps of:

initially positioning the elongate stiffening member in the first lumen of the first catheter during positioning of the first catheter in the carotid artery; and withdrawing the elongate stiffening member to permit inflating the first balloon.

4. A method according to claim 1 further comprising the step of providing the elongate stiffening member to have an enlarged diameter portion at a predetermined location; and wherein the step of positioning the elongate stiffening member comprises positioning same to seal a proximal end of the first lumen of the first catheter with the enlarged diameter portion.

5. A method according to claim 4 wherein the step of providing the elongate stiffening member comprises providing a metallic wire.

6. A method according to claim 1 wherein the second catheter carries a stent at the distal end thereof; and wherein the steps of inflating the second balloon and placing the stent are performed simultaneously.

7. A method according to claim 1 further comprising the steps of:
deflating the second balloon while cerebral protection is maintained by the inflated first balloon; and
withdrawing the second catheter while cerebral protection is maintained by the inflated first balloon.

8. A method according to claim 7 wherein the step of placing the stent comprises the steps of:
providing a third catheter carrying a stent at a distal end thereof;
positioning the stent adjacent the expanded stenosis by sliding the third catheter over the catheter guide while cerebral protection is maintained by the inflated first balloon;
expanding the stent at the expanded stenosis while cerebral protection is maintained by the inflated first balloon; and
withdrawing the third catheter while cerebral protection is maintained by the inflated first balloon.

9. A method according to claim 8 wherein the step of providing the third catheter comprises providing same comprising a third balloon carrying the stent; and wherein the step of expanding the stent comprises inflating the third balloon.

10. A method according to claim 8 wherein the step of providing the third catheter carrying the stent comprises providing the third catheter carrying a self-expanding stent; and wherein the step of expanding the stent comprises releasing the self-expanding stent.

11. A method according to claim 1 further comprising the step of performing at least one of suction and lavage at the stenosis, after placing the stent and prior to deflating the first balloon, to thereby remove any debris while cerebral protection is maintained by the inflated first balloon.

12. A method according to claim 11 wherein the step of performing at least one of suction and lavage comprises the steps of:
providing a fourth catheter having at least one opening at a distal end thereof;
positioning the distal end of the fourth catheter adjacent the stenosis by sliding the fourth catheter over the catheter guide; and
performing at least one of applying suction and injecting fluid through the at least one opening of the fourth catheter.

13. A method according to claim 1 wherein the step of positioning the first catheter further comprises the steps of:
providing an introduction catheter having a lumen and positioning a distal end of the introduction catheter adjacent the stenosis; and
inserting the first catheter through the lumen of the introduction catheter.

14. A method according to claim 13 further comprising the step of removing the introduction catheter after inflating the first balloon.

15. A method according to claim 1 further comprising the step of predilatating the stenosis prior to positioning the first catheter.

16. An endovascular method for treating a stenosis of a carotid artery of a patient, the method comprising the steps of:
providing a first catheter comprising a first balloon at a distal end thereof, the catheter having a first lumen therein;
positioning the first catheter in the carotid artery of the patient so that the first balloon is downstream from the stenosis;
inflating the first balloon in the carotid artery downstream from the stenosis to block the carotid artery to provide cerebral protection for the patient;
inserting an elongate stiffening member in the first lumen of the first catheter after inflating the first balloon to stiffen the first catheter to define a catheter guide;
providing a second catheter carrying a stent at a distal end thereof and placing the stent at the stenosis by sliding the second catheter over the catheter guide while cerebral protection is maintained by the inflated first balloon; and
deflating the first balloon and withdrawing the first catheter from the patient.

17. A method according to claim 16 wherein the first lumen is in fluid communication with the first balloon, and wherein the step of positioning the elongate stiffening member also seals the inflated first balloon.

18. A method according to claim 16 wherein the step of placing the stent comprises sliding the second catheter over the first catheter.

19. A method according to claim 16 further comprising the step of expanding the stenosis.

20. A method according to claim 19 wherein the step of expanding the stenosis is performed prior to placing the stent.

21. A method according to claim 19 wherein the step of expanding the stenosis is performed while placing the stent.

22. A method according to claim 19 wherein the step of expanding the stenosis comprises the steps of providing a third catheter having a third balloon at a distal end thereof, positioning the third catheter over the first catheter, and inflating the third balloon to expand the stenosis.

23. A method according to claim 16 further comprising the step of performing at least one of suction and lavage at the stenosis, after placing the stent and prior to deflating the first balloon, to thereby remove debris.

24. A method according to claim 20 wherein the step of performing at least one of suction and lavage comprises the steps of:
providing a fourth catheter having at least one opening at a distal end thereof;
positioning the distal end of the fourth catheter adjacent the stenosis by sliding the fourth catheter over the first catheter; and
performing at least one of applying suction and injecting fluid through the at least one opening of the fourth catheter.

25. A method according to claim 16 wherein the step of positioning the first catheter further comprises the steps of:
providing an introduction catheter having a lumen and positioning a distal end of the introduction catheter adjacent the stenosis;

inserting the first catheter through the lumen of the introduction catheter.

26. A method according to claim 25 further comprising the step of removing the introduction catheter after inflating the first balloon.

27. A method according to claim 16 further comprising the step of predilatating the stenosis prior to positioning the first catheter.

* * * * *